(12) United States Patent
Barbour et al.

(10) Patent No.: US 10,852,309 B2
(45) Date of Patent: Dec. 1, 2020

(54) METHODS FOR DETECTING PHOSPHORYLATED ALPHA-SYNUCLEIN

(71) Applicant: PROTHENA BIOSCIENCES LIMITED, Dublin (IE)

(72) Inventors: Robin Barbour, Walnut Creek, CA (US); Lynn R. Zieske, Livermore, CA (US); Sarah Hamren, Martinez, CA (US)

(73) Assignee: PROTHENA BIOSCIENCES LIMITED, Dublin (IE)

( * ) Notice: Subject to any disclaimer, the term of this patent is extended or adjusted under 35 U.S.C. 154(b) by 0 days.

(21) Appl. No.: 15/247,598

(22) Filed: Aug. 25, 2016

(65) Prior Publication Data

US 2017/0192017 A1    Jul. 6, 2017

Related U.S. Application Data

(60) Provisional application No. 62/297,777, filed on Feb. 19, 2016, provisional application No. 62/209,800, filed on Aug. 25, 2015.

(51) Int. Cl.
| | |
|---|---|
| *G01N 33/68* | (2006.01) |
| *C07K 16/18* | (2006.01) |
| *G01N 33/50* | (2006.01) |
| *G01N 33/58* | (2006.01) |
| *G01N 33/543* | (2006.01) |

(52) U.S. Cl.
CPC ......... *G01N 33/6896* (2013.01); *C07K 16/18* (2013.01); *G01N 33/502* (2013.01); *G01N 33/54326* (2013.01); *G01N 33/58* (2013.01); *G01N 33/582* (2013.01); *C07K 2317/24* (2013.01); *C07K 2317/565* (2013.01); *G01N 2333/435* (2013.01); *G01N 2800/2814* (2013.01)

(58) Field of Classification Search
CPC .. G01N 33/6896; G01N 33/502; G01N 33/58; G01N 33/54326; G01N 33/582; G01N 2333/435; G01N 2800/2814; C07K 16/18; C07K 2317/24; C07K 2317/565
See application file for complete search history.

(56) References Cited

U.S. PATENT DOCUMENTS

| | | |
|---|---|---|
| 7,674,599 B2 | 3/2010 | Chilcote et al. |
| 7,910,333 B2 | 3/2011 | Chilcote et al. |
| 8,673,593 B2 | 3/2014 | Chilcote et al. |
| 2005/0196818 A1* | 9/2005 | Chilcote ................ C07K 16/18 435/7.93 |
| 2010/0031377 A1 | 2/2010 | Schenk et al. |
| 2013/0317199 A1 | 11/2013 | Chilcote et al. |

FOREIGN PATENT DOCUMENTS

| | | | |
|---|---|---|---|
| WO | WO 2005/047860 A2 | 5/2005 | |
| WO | WO 2006/020581 A2 | 2/2006 | |
| WO | WO-2009033743 A1 * | 3/2009 | ............. C07K 16/18 |
| WO | WO 2017/033152 A1 | 3/2017 | |

OTHER PUBLICATIONS

Anderson, et al., "Phosphorylation of Ser-129 Is the Dominant Pathological Modification of α-Synuclein in Familial and Sporadic Lewy Body Disease, Methods for Detecting Phosphorylated Alpha-Synuclein," *The Journal of Biological Chemistry*, vol. 281, No. 40, pp. 29739-29752, (Oct. 6, 2006)
Games, et al., "Reducing C-Terminal-Truncated Alpha-Synuctein by Immunotherapy Attenuates Neurodegeneration and Propagation in Parkinson's Disease-Like Models," *The Journal of Neuroscience*, 34(28):9441-9454, (Jul. 9, 2014).
Lim, et al., "α-Syn suppression Reverses Synaptic and Memory Defects in a Mouse Model of Dementia with Lewy Bodies," *The Journal of Neuroscience*, 31(27):10076-10087, (Jul. 6, 2011).
Nasstrom, et al., "Antibodies against Alpha-Synuclein Reduce Oligomerization in Living Cells," *PLoS ONE*, vol. 6, Issue 10, e27230, (Oct. 2011).
PCT/IB2016/055088 International Search Report dated Dec. 13, 2016.
PCT/IB2016/055088 Written Opinion dated Dec. 13, 2016.
Shukla, et al., "Quantitative determination of human interleukin 22 (IL-22) in serum using Singulex-Erenn® Technology," *Journal of Immunological Methods*, 390:30-34, (2013).
Todd, et al., "Ultrasensitive Flow-based Immunoassays Using Single-Molecule Counting," *Clinical Chemistry*, 53:11, pp. 1990-1995, (2007).
Yang, et al., "A highly sensitive novel immunoassay specifically detects low levels of soluble Aβ oligomers in human cerebrospinal fluid," *Alzheimer's Research Therapy*, 7:14, (2015).
Yeung, et al., "Evaluation of highly sensitive immunoassay technologies for quantitative measurements of sub-pg/mL levels of cytokines in human serum," *Journal of Immunological Methods*, 427, pp. 53-63, (2016).
PCT/IB2016/055088 International Preliminary Report on Patentability dated Feb. 27, 2018.

* cited by examiner

*Primary Examiner* — Gregory S Emch
(74) *Attorney, Agent, or Firm* — Alston & Bird LLP

(57) ABSTRACT

The invention provides methods of detecting alpha-synuclein using a capture antibody and a reporter antibody. The capture antibody binds preferentially to full-length alpha-synuclein phosphorylated at residue 129 (PS129 alpha-synuclein) over unphosphorylated full-length alpha-synuclein. The 11A5 antibody is an example of a suitable capture antibody. The reporter antibody binds to an epitope within residues 40-55 of alpha-synuclein. The 23E8 antibody is an example of such an antibody. Because only a small proportion of alpha-synuclein is phosphorylated high sensitivity of detection below picomolar is advantageous.

38 Claims, 3 Drawing Sheets
Specification includes a Sequence Listing.

| Standard | Expected [PS129] pg/mL | n | Mean [PS129] pg/mL | SD | CV% | Recovery |
|---|---|---|---|---|---|---|
| 1 | 25.00 | 3 | 24.79 | 1.57 | 6 | 99% |
| 2 | 12.50 | 3 | 13.15 | 0.75 | 6 | 105% |
| 3 | 6.25 | 3 | 6.31 | 0.32 | 5 | 101% |
| 4 | 3.13 | 3 | 3.04 | 0.36 | 12 | 97% |
| 5 | 1.56 | 3 | 1.56 | 0.02 | 1 | 100% |
| 6 | 0.78 | 3 | 0.77 | 0.12 | 16 | 98% |
| 7 | 0.39 | 3 | 0.42 | 0.04 | 10 | 108% |
| 8 | 0.20 | 2 | 0.21 | 0.00 | 0 | 107% |
| 9 | 0.10 | 3 | 0.10 | 0.02 | 19 | 103% |
| 10 | 0.05 | 3 | 0.04 | 0.00 | 10 | 80% |
| 11 | 0.02 | 3 | ND | – | – | – |
| 12 | 0.00 | 2 | ND | – | – | – |

| Standard | Expected [PS129] pg/mL | n | DE Mean | SD | CV% |
|---|---|---|---|---|---|
| 6 | 0.78 | 3 | 1011 | 156 | 15 |
| 7 | 0.39 | 3 | 573 | 51 | 9 |
| 8 | 0.20 | 2 | 324 | 1 | 0 |
| 9 | 0.10 | 3 | 207 | 21 | 10 |
| 10 | 0.05 | 3 | 142 | 4 | 3 |
| 11 | 0.02 | 3 | 108 | 13 | 12 |
| 12 | 0.00 | 2 | 106 | 5 | 5 |

| Standard | Expected [p-α-synuclein] pg/mL | n | Mean [p-α-synuclein] pg/mL | SD | CV% | Recovery |
|---|---|---|---|---|---|---|
| 1 | 50.00 | 3 | 45.69 | 2.14 | 5 | 91% |
| 2 | 25.00 | 3 | 27.41 | 1.83 | 7 | 110% |
| 3 | 12.50 | 3 | 13.32 | 0.98 | 7 | 107% |
| 4 | 6.25 | 3 | 6.39 | 0.77 | 12 | 102% |
| 5 | 3.13 | 3 | 3.30 | 0.54 | 16 | 106% |
| 6 | 1.56 | 3 | 1.37 | 0.01 | 0 | 88% |
| 7 | 0.78 | 3 | 0.77 | 0.03 | 4 | 98% |
| 8 | 0.39 | 3 | 0.43 | 0.04 | 10 | 109% |
| 9 | 0.20 | 3 | 0.21 | 0.02 | 10 | 109% |
| 10 | 0.10 | 3 | 0.11 | 0.02 | 15 | 109% |
| 11 | 0.05 | 3 | 0.04 | 0.00 | 11 | 78% |
| 12 | 0.00 | 2 | ND | — | — | — |

| Standard | Expected [p-α-synuclein] pg/mL | n | DE Mean | SD | CV% |
|---|---|---|---|---|---|
| 7 | 0.78 | 3 | 1317 | 43 | 3 |
| 8 | 0.39 | 3 | 784 | 65 | 8 |
| 9 | 0.20 | 3 | 443 | 32 | 7 |
| 10 | 0.10 | 3 | 276 | 25 | 9 |
| 11 | 0.05 | 3 | 163 | 7 | 4 |
| 12 | 0.00 | 2 | 88 | 11 | 13 |

METHODS FOR DETECTING PHOSPHORYLATED ALPHA-SYNUCLEIN

CROSS REFERENCE TO RELATED APPLICATIONS

The present application claims the benefit of US Provisional Application Nos. 62/297,777 filed Feb. 19, 2016, and 62/209,800 filed Aug. 25, 2015, which are incorporated by reference in its entirety.

REFERENCE TO A SEQUENCE LISTING

This application incorporates by reference the Sequence Listing submitted in Computer Readable Form as file 719US_SEQLST.txt, created on Aug. 25, 2016, and containing 1608 bytes.

BACKGROUND

Alpha-synuclein brain pathology is a conspicuous feature of several neurodegenerative diseases termed synucleinopathies. Alpha-synuclein is the main component of Lewy bodies (LBs) and Lewy neurites, which are intraneuronal inclusions.

Synucleinopathies include Parkinson's disease (PD), dementia with Lewy bodies (DLB), the Lewy body variant of Alzheimer's disease (LBVAD), diffuse Lewy body disease (DLBD), multiple systems atrophy (MSA), and neurodegeneration with brain iron accumulation type-1 (NBIA-1).

Synucleinopathies are a common cause for movement disorders and cognitive deterioration in the aging population (Galasko et al., Arch. Neurol. (1994) 51:888-95). To date these disorders are neither curable nor preventable and understanding the causes and pathogenesis of PD is critical towards developing new treatments (Tanner et al., Curr. Opin. Neurol. (2000) 13:427-30). The cause for PD is controversial and multiple factors have been proposed to play a role, including various neurotoxins and genetic susceptibility factors.

Several studies have shown that alpha-synuclein plays a central role in PD pathogenesis because: (1) this protein accumulates in LBs (Spillantini et al., Nature (1997) 388: 839-40; Takeda et al., J. Pathol. (1998) 152:367-72; Wakabayashi et al., Neurosci. Lett. (1997) 239:45-8), (2) mutations in the alpha-synuclein gene co-segregate with rare familial forms of Parkinsonism (Kruger et al., Nature Gen. (1998) 18:106-8; Polymeropoulos et al., Science (1997) 276:2045-7) and, (3) its overexpression in transgenic mice (Masliah et al., Science (2000) 287:1265-9) and *Drosophila* (Feany et al., Nature (2000) 404:394-8) mimics several pathological aspects of PD. Thus, the fact that accumulation of alpha-synuclein in the brain is associated with similar morphological and neurological alterations in species as diverse as humans, mice, and flies suggests that this molecule contributes to the development of PD.

Synuclein phosphorylated at residue serine 129 (PS129) has been reported as a pathological modification of alpha-synuclein found in Lewy Bodies and Lewy neurites in PD and in other synucleinopathies such as Lewy-body dementia and Multiple System Atrophy (Anderson et al. J. Biol. Chem. 281:29739-29752 (2006)). Although levels of total alpha-synuclein levels in cerebrospinal fluid have been reported to be decreased in synucleinopathic disease, there is substantial overlap between levels in subjects with and without disease (Kang et. AL JAMA Neurol. 70(10): 1277-1287 (2013)). CSF levels of PS129 and ratios of PS129 to total alpha-synuclein have been reported to be increased in Parkinson's patients relative to controls (Wang et al Sci Transl Med. 2012 Feb. 15; 4(121): 121).

SUMMARY OF THE CLAIMED INVENTION

The invention provides a method of detecting alpha-synuclein phosphorylated at serine 129 (PS129 alpha-synuclein), comprising: contacting a sample with a capture antibody that preferentially binds to PS129 alpha-synuclein and a reporter antibody that specifically binds to an epitope within residues 40-55 of alpha-synuclein; wherein if PS129 alpha-synuclein is present in the sample, the capture antibody and reporter antibody bind to the PS129 alpha-synuclein forming a sandwich complex; and detecting the reporter antibody that binds to the PS129-alpha synuclein in step (a), if any, to indicate presence or absence of the PS129 alpha-synuclein.

Optionally, the capture antibody is 11A5 and the report antibody is 23E8. Optionally, the capture antibody is attached to the support via a linker. Optionally, the method further comprises eluting the reporter antibody from the sandwich complex before detecting the reporter antibody. Optionally, the reporter antibody is fluorescently labeled, and is detected by single-molecule counting. Optionally, the sample is contacted with the capture antibody, the capture antibody binds to PS129 alpha-synuclein, the capture antibody bound to PS129 alpha-synuclein is separated from other components of the sample and resuspended in solution, which is contacted with the reporter antibody, which binds to the PS129 alpha-synuclein forming the sandwich complex, which is separated from other components of the resuspended solution, and the reporter antibody is eluted from the sandwich complex and detected. Optionally, the method is performed qualitatively. Optionally, the method is performed quantitatively to indicate an absolute or relative amount of the PS129 alpha-synuclein. Optionally, the sample contains 0.1-1.0 M guanidine. Optionally, the sample contains 0.5 M guanidine. Optionally, the capture antibody is bound to a solid phase before the contacting step. Optionally, the solid phase is magnetic beads. Optionally, the capture antibody is attached to magnetic beads, which are separated from the remainder of the sample or resuspended solution by applying a magnetic field.

Optionally, the method further comprises comparing a signal from the reporter antibody with a signal from the reporter antibody in a control sample containing a known amount of PS129 alpha-synuclein to determine the amount of PS129 alpha-synuclein in the sample. Optionally, the method further comprises comparing a signal from the reporter antibody from a calibration curve of signal versus amount of PS129 alpha-synuclein to determine the amount of PS129 alpha-synuclein in the sample. Optionally, a signal from the reporter antibody is proportional to the amount of PS129 alpha-synuclein in the sample. Optionally, the method further comprises contacting the reporter antibody with a labeled antibody to generate a signal indicating presence of the reporter antibody and thereby presence of PS129 alpha-synuclein in the sample. Optionally, the method further comprises determining a level of total alpha-synuclein or unphosphorylated alpha-synuclein in the sample and calculating a ratio of the level of phosphorylated alpha-synuclein to the level of total alpha-synuclein or unphosphorylated alpha-synuclein.

Optionally, the sample is diluted in Singulex standard diluent comprising 0.1% Triton X-405. Optionally, the sample is a sample from a human. Optionally, the sample from a transgenic mouse with a transgene expressing human alpha-synuclein. Optionally, the sample is a body fluid. Optionally, the sample is cerebrospinal fluid (CSF) of a human. Optionally, the CSF sample is diluted 1:4 in Singulex standard diluent comprising 0.1% Triton X-405. Optionally, there is no cross-reactivity with synuclein monomer at up to 500 pg/mL. Optionally, the CSF sample comprises <500 ng/mL hemoglobin. Optionally, the CSF sample comprises 200 ng/mL to 500 ng/mL hemoglobin. Optionally, the CSF sample comprises <200 ng/mL hemoglobin.

Optionally, the sample is a brain homogenate of a human or transgenic animal. Optionally, the sample is a medium used to culture cells. Optionally, the cells express recombinant human alpha-synuclein. Optionally, the method detects presence of PS129 alpha-synuclein at a level of 0.1 pg/mL. Optionally, the method detects presence of PS129 alpha-synuclein at a level of at least 0.4 pg/mL. Optionally, presence of PS129-alpha-synuclein is used to diagnose a subject from whom the sample was obtained with Lewy body disease.

Some methods are performed multiple times on a subject with Lewy body disease, wherein the amount of PS129 alpha-synuclein decreases with time indicating reduced severity of Lewy body disease. Optionally, the method is performed multiple times on a subject with Lewy body disease, wherein the amount of PS129 alpha-synuclein increases with time indicating increased severity of Lewy body disease. Optionally, the subject is receiving immunotherapy for the Lewy body disease.

Optionally, the method is performed on a population of subjects, wherein a greater proportion of subjects with presence of PS129 alpha-synuclein thereafter receive a treatment for Lewy body disease than subjects with absence of PS129-alpha synuclein. Optionally, the method is performed on a population of subjects, wherein a greater proportion of subject with a level of PS129 alpha-synuclein at or exceeding a threshold receive treatment for a Lewy body disease than subjects in which the level of PS129 alpha-synuclein is below the threshold.

The invention further provides a monoclonal antibody comprising the Kabat CDRs of 23E8 (ATCC accession number PTA-122711). Optionally, the monoclonal antibody is chimeric, veneered or humanized.

DEFINITIONS

Figures 1, 2A, 2B:
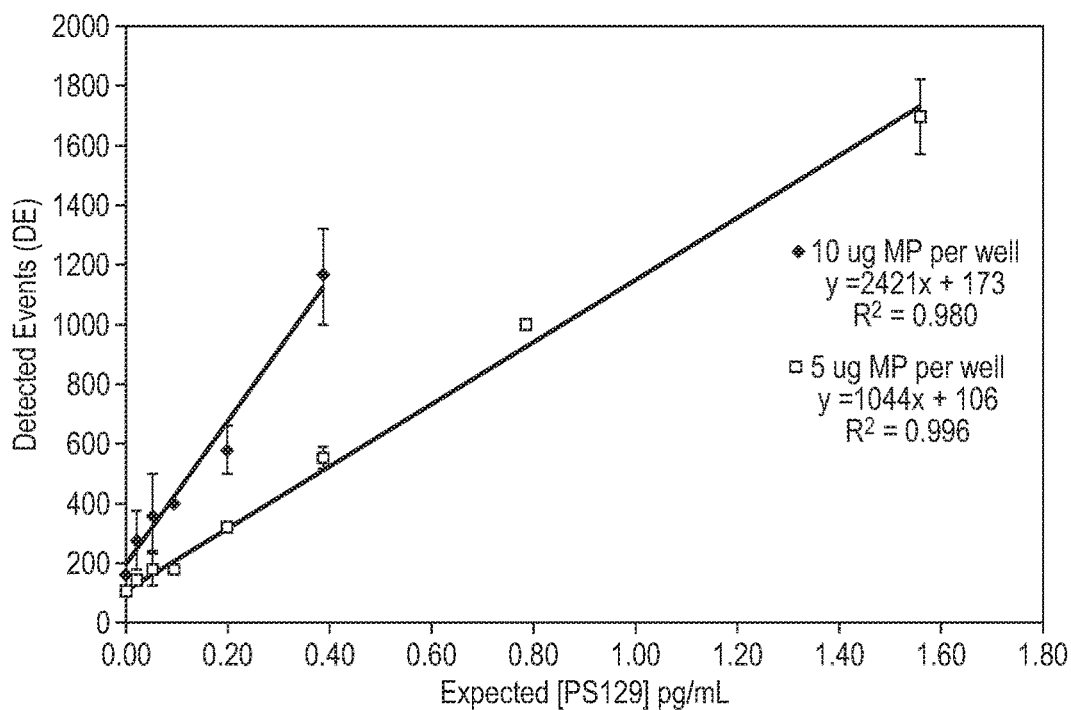
FIG. 1 shows sensitivity of detection 11A5 as the capture antibody and 23E8 as the reporter antibody with different amounts of the capture antibody in the wells.
FIGS. 2A-C: show determination, in an assay using Singulex standard diluent, of a calibration curve relating signal to PS129 alpha-synuclein concentration (A) 12 point PS129 alpha-synuclein standard curve, B low end plotting actual values (mean detection events) and C, linear plot.

The phrase that an antibody "specifically binds" to a target refers to a binding reaction which is determinative of the presence of the antibody in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. Specific binding between two entities means an affinity of at least $10^6$, $10^7$, $10^8$, $10^9$ or $10^{10}$ M$^{-1}$. Affinities greater than $10^8$ M$^{-1}$ are preferred. Lack of specific binding means binding to a target indistinguishable from an irrelevant control antibody and/or an affinity of less than $10^6$M$^{-1}$.

The term "antibody" includes intact antibodies and binding fragments thereof. Typically, fragments compete with the intact antibody from which they were derived for specific binding to an antigen fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992).

Antibodies of the invention are typically substantially pure from undesired contaminant. This means that an agent is typically at least about 50% w/w (weight/weight) purity, as well as being substantially free from interfering proteins and contaminants. Sometimes the antibodies are at least about 80% w/w and, more preferably at least 90 or about 95% w/w purity. However, using conventional protein purification techniques, homogeneous antibodies of at least 99% w/w can be obtained.

The term "epitope" or "antigenic determinant" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids or post-translationally modified amino acids are typically retained on exposure to denaturing solvents whereas epitopes formed by tertiary folding are typically lost on treatment with denaturing solvents. An epitope typically includes at least 3, but generally speaking 5-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996). Antibodies that recognize the same epitope can be identified in a simple immunoassay showing the ability of one antibody to block the binding of another antibody to a target antigen.

The term "body fluid" refers to those fluids of a mammalian host which is suspected contain measurable amounts of alpha-synuclein or fragments thereof, specifically including blood, cerebrospinal fluid (CSF), urine, and peritoneal fluid. The term "blood" refers to whole blood, as well as blood plasma and serum.

A synucleinopathic disease means a disease characterized by Lewy bodies, Lewy neurites or other deposits of alpha-synuclein.

Qualitative assay detects presence or absence of an analyte. A quantitative assay detects not only presence or absence of the analyte but if present provides an absolute or relative amount of the analyte.

Immunotherapy against alpha-synuclein means inducing an active or passive immune response against alpha-synuclein, such as by administering an immunogenic alpha-synuclein peptide to induce an antibody against alpha-synuclein or administering an antibody against alpha-synuclein.

Compositions or methods "comprising" one or more recited elements may include other elements not specifically recited. For example, a composition that comprises alpha-synuclein peptide encompasses both an isolated alpha-synuclein peptide and alpha-synuclein peptide as a component of a larger polypeptide sequence.

DETAILED DESCRIPTION

The invention provides methods for detecting PS129 alpha-synuclein in samples. Because PS129 alpha-synuclein typically constitutes only a small fraction of total alpha-synuclein in such samples, a high sensitivity of detection below picomolar is advantageous.

I. Antibodies Used in Detection

The invention provides methods of detecting alpha-synuclein using a capture antibody and a reporter antibody. The capture antibody binds preferentially to full-length alpha-synuclein phosphorylated at residue 129 (PS129 alpha-synuclein) over unphosphorylated full-length alpha-synuclein. Preferential binding means an association constant at least five times higher for PS129 alpha-synuclein than unphosphorylated alpha-synuclein. Optionally the association constant is at least ten times higher for PS129 alpha-synuclein than unphosphorylated alpha-synuclein. Optionally, the antibody lacks specific binding to unphosphorylated alpha-synuclein. The 11A5 antibody is an example of a suitable capture antibody.

The reporter antibody binds to an epitope within residues 40-55 of alpha-synuclein. The 23E8 antibody is an example of such an antibody. Various other antibodies are used as controls in the examples.

The cell line designated JH22.11A5.6.29.70.54.16.14, producing the antibody 11A5 having the ATCC accession number PTA-8222 has been deposited on Feb. 26, 2007 at the ATCC. The cell line designated JH19.23E8.2.32.22, producing the antibody 23E8 having the ATCC accession number PTA-122711 has been deposited on Dec. 9, 2015 at the ATCC. The invention further provides humanized and chimeric forms of mouse monoclonals, particularly those described above.

When an antibody is said to bind to an epitope within specified residues, such as alpha-synuclein 40-55, for example, what is meant is that the antibody specifically binds to a polypeptide consisting of the specified residues (i.e., alpha-synuclein 40-55 in this an example). Such an antibody does not necessarily contact every residue within alpha-synuclein 40-55. Nor does every single amino acid substitution or deletion within alpha-synuclein 40-55 necessarily significantly affect binding affinity. Epitope specificity of an antibody can be determined, for example, by testing a collection of overlapping peptides of about 15 amino acids spanning the sequence of alpha-synuclein and differing in increments of a small number of amino acids (e.g., 3 amino acids). The peptides are immobilized within the wells of a microtiter dish. Immobilization can be effected by biotinylating one terminus of the peptides. Optionally, different samples of the same peptide can be biotinylated at the N and C terminus and immobilized in separate wells for purposes of comparison. Such is particularly useful for identifying end-specific antibodies. An antibody is screened for specific binding to each of the various peptides. The epitope is defined as occurring within a segment of amino acids that is common to all peptides to which the antibody shows specific binding.

i. General Characteristics of Immunoglobulins

The basic antibody structural unit is known to comprise a tetramer of subunits. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, Fundamental Immunology, Paul, W., ed., 2nd ed. Raven Press, N.Y., 1989, Ch. 7 (incorporated by reference in its entirety for all purposes).

The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md., 1987 and 1991); Chothia & Lesk, J. Mol. Biol. 196:901-917 (1987); or Chothia et al., Nature 342:878-883 (1989).

ii. Production of Nonhuman Antibodies

Mouse or other non-human antibodies can be produced by conventional hybridoma technology. The desired binding specificity can be imparted by selection of the immunogen and/or the screening approach. For generating antibodies with an epitope specificity between residues 40 and 55, a fragment of alpha-synuclein consisting of these residues (i.e., 40-55) can be used an immunogen or a longer fragment including these residues up to full-length alpha-synuclein. Antibodies can be screened by binding to overlapping peptides as described above. For producing an antibody preferentially binding to PS129 alpha-synuclein, full length PS129 alpha synuclein or a fragment thereof including residue 129 and sufficient residues either side to constitute an epitope (e.g., 3-15 contiguous residues including residue 129) can be used as the immunogen. Antibodies are screened for preferential binding to PS129 alpha-synuclein against unphosphorylated alpha-synuclein.

Chimeric and humanized antibodies have the same or similar binding specificity and affinity as a mouse or other nonhuman antibody that provides the starting material for construction of a chimeric or humanized antibody. Chimeric antibodies are antibodies whose light and heavy chain genes have been constructed, typically by genetic engineering, from immunoglobulin gene segments belonging to different species. For example, DNA encoding the variable domains of a mouse antibody can be sequenced, and DNA construct(s) encoding the variable domains joined to human constant (C) segments, such as IgG1 and IgG4 constructed. The constructs are then expressed to produce the antibody Human isotype IgG1 is preferred. In some methods, the isotype of the antibody is human IgG1. IgM antibodies can also be used in some methods. A typical chimeric antibody is thus a hybrid protein consisting of the V or antigen-binding domain from a mouse antibody and the C or effector domain from a human antibody.

Humanized antibodies have variable region framework residues substantially from a human antibody or consensus of human antibodies (termed an acceptor antibody) and some and usually all six complementarity determining regions substantially or entirely from a mouse-antibody, (referred to as the donor immunoglobulin). See, Queen et al., Proc. Natl. Acad. Sci. USA 86:10029-10033 (1989), WO 90/07861, U.S. Pat. Nos. 5,693,762, 5,693,761, 5,585,089, 5,530,101, and Winter, U.S. Pat. No. 5,225,539 (each of which is incorporated by reference in its entirety for all purposes). The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See Carter et al., WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid should usually be substituted by the equivalent framework amino acid from the mouse antibody when it is reasonably expected that the amino acid: (1) noncovalently binds antigen directly, (2) is adjacent to a CDR region, (3) otherwise interacts with a CDR region (e.g. is within about 6 A of a CDR region), or (4) participates in the VL-VH interface.

Other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins. Other candidates for substitution are acceptor human framework amino acids that are unusual for a human immunoglobulin at that position. The variable region frameworks of humanized immunoglobulins usually show at least 85% sequence identity to a human variable region framework sequence or consensus of such sequences.

iii. Human Antibodies

Human antibodies against alpha-synuclein are provided by a variety of techniques described below. Human antibodies can also be screened for a particular epitope specificity by using only a fragment of alpha-synuclein as the immunogen, and/or by screening antibodies against a collection of deletion mutants of alpha-synuclein. Human antibodies preferably have isotype specificity human IgG1. Several methods are available for producing human antibodies including the trioma method, Oestberg et al., Hybridoma 2:361-367 (1983); Oestberg, U.S. Pat. No. 4,634,664; and Engleman et al., U.S. Pat. No. 4,634,666 (each of which is incorporated by reference in its entirety for all purposes); transgenic non-human mammals described in detail by, e.g., Lonberg et al., WO93/1222, U.S. Pat. Nos. 5,877,397, 5,874,299, 5,814,318, 5,789,650, 5,770,429, 5,661,016, 5,633,425, 5,625,126, 5,569,825, 5,545,806, Nature 148, 1547-1553 (1994), Nature Biotechnology 14, 826 (1996), Kucherlapati, WO 91/10741 (each of which is incorporated by reference in its entirety for all purposes); and phage display methods See, e.g., Dower et al., WO 91/17271 and McCafferty et al., WO 92/01047, U.S. Pat. Nos. 5,877,218, 5,871,907, 5,858,657, 5,837,242, 5,733,743 and 5,565,332 (each of which is incorporated by reference in its entirety for all purposes).

iv. Selection of Constant Region

The heavy and light chain variable regions of chimeric, humanized, or human antibodies can be linked to at least a portion of a human constant region. The choice of constant region depends, in part, whether antibody-dependent complement and/or cellular mediated toxicity is desired. For example, isotypes IgG1 and IgG3 have complement activity and isotypes IgG2 and IgG4 do not. Choice of isotype can also affect passage of antibody into the brain. Human isotype IgG1 is preferred. Light chain constant regions can be lambda or kappa. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

v. Expression of Recombinant Antibodies

Chimeric, humanized and human antibodies are typically produced by recombinant expression. Recombinant polynucleotide constructs typically include an expression control sequence operably linked to the coding sequences of antibody chains, including naturally associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences.

*E. coli* is one prokaryotic host particularly useful for cloning the DNA sequences of the present invention. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells are a preferred host for expressing nucleotide segments encoding immunoglobulins or fragments thereof. See Winnacker, From Genes to Clones, (VCH Publishers, N Y, 1987). A number of suitable host cell lines capable of secreting intact heterologous proteins have been developed in the art, and include CHO cell lines, various COS cell lines, HeLa cells, L cells, human embryonic kidney cell, and myeloma cell lines. Preferably, the cells are non-human. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., J. Immunol. 148:1149 (1992).

Alternatively, antibody coding sequences can be incorporated in transgenes for introduction into the genome of a transgenic animal and subsequent expression in the milk of the transgenic animal (see, e.g., U.S. Pat. Nos. 5,741,957, 5,304,489, 5,849,992). Suitable transgenes include coding sequences for light and/or heavy chains in operable linkage with a promoter and enhancer from a mammary gland specific gene, such as casein or beta lactoglobulin.

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

Once expressed, antibodies can be purified according to standard procedures of the art, including HPLC purification, column chromatography, and gel electrophoresis and the like (see generally, Scopes, Protein Purification (Springer-Verlag, N.Y., 1982).

II. Alpha-Synuclein

Alpha-synuclein was originally identified in human brains as the precursor protein of the non-.beta.-amyloid component of (NAC) of AD plaques. (Ueda et al., Proc. Natl. Acad. Sci. U.S.A. 90 (23):11282-11286 (1993). Alpha-synuclein, also termed the precursor of the non-Aβ component of AD amyloid (NACP), is a peptide of 140 amino acids. Full-length alpha-synuclein has the amino acid sequence:

```
(Ueda et al., Ibid.; GenBank accession number:
P37840)
                                         (SEQ ID NO: 1)
MDVFMKGLSKAKEGVVAAAEKTKQGVAEAAGKTKEGVLYVGSKTKEGVVH

GVATVAEKTKEQVTNVGGAVVTGVTAVAQKTVEGAGSIAAATGFVKKDQL

GKNEEGAPQEGILEDMPVDPDNEAYEMPSEEGYQDYEPEA.
```

Unless otherwise indicated, reference to alpha-synuclein means the natural human amino acid sequence indicated above as well as natural allelic and species variants thereof, including full-length forms and fragments thereof found in samples being analyzed, as well as forms having undergone posttranslational modification, such as phosphorylation. Fragments or variants of alpha-synuclein are numbered as in the exemplified sequences such that aligned residues are allocated the same number.

III. Assays for Detecting Alpha Synuclein

Alpha-synuclein can be detected by sandwich immunoassays (see U.S. Pat. Nos. 4,376,110, 4,486,530, 5,914,241, and 5,965,375) in which one antibody is immobilized to a solid phase (capture antibody), and another antibody in solution (reporter antibody). Typically, the reporter antibody is labeled, either directly or via a secondary labeling reagent, such as an antiidiotypic antibody. The capture and reporter antibodies having different binding specificities so both can bind to alpha-synuclein at the same time. Capture and reporter antibodies can be contacted with target antigen in either order or simultaneously. If the capture antibody is contacted first, the assay is referred to as being a forward assay. Conversely, if the reporter antibody is contacted first, the assay is referred to as being a reverse assay. If target is contacted with both antibodies simultaneously, the assay is referred to as a simultaneous assay. After contacting the target with antibody, a sample is incubated for a period that can vary from about 10 min to about 24 hr, but typically is about 1-2 hr. A wash step can be performed to remove components of the sample that do not become specifically bound to the solid phase. When capture and reporter antibodies are bound in separate steps, a wash can be performed after either or both binding steps. After washing, the reporter antibody is detected. The reporter antibody can be detected while part of a sandwich complex of capture antibody, PS129 alpha-synuclein reporter antibody or after elution from such a sandwich complex. The reporter antibody can be labelled directly or indirectly via a secondary labelled antibody binding to the reporter antibody. Usually for a given pair of capture and reporter antibodies, a calibration curve is prepared from samples containing known concentrations of target antigen. Concentrations of antigen in samples being tested are then read by interpolation from the calibration curve. Analyte can be measured either from the amount of labeled reporter antibody binding at equilibrium or by kinetic measurements from bound labeled solution antibody at a series of time points before equilibrium is reached. The slope of such a curve is a measure of the concentration of target in a sample. Alternatively, the amount of alpha-synuclein in a sample can be determined by comparing the signal of reporter antibody from binding to alpha-synuclein the sample with the signal from reporter antibody from binding to a known amount of alpha-synuclein in a control sample.

Suitable detectable labels for use in the above methods include any moiety that is detectable by spectroscopic, photochemical, biochemical, immunochemical, electrical, optical, chemical, or other means. For example, suitable labels include biotin for staining with labeled streptavidin conjugate, fluorescent dyes (e.g., fluorescein, Texas red, rhodamine, green fluorescent protein, and the like), radiolabels (e.g., $^3$H, $^{12}$S, $^{35}$S, $^{14}$C or $^{32}$P), enzymes (e.g., horseradish peroxidase, alkaline phosphatase and others commonly used in an ELISA), and colorimetric labels such as colloidal gold or colored glass or plastic (e.g., polystyrene, polypropylene, latex beads). Patents that described the use of such labels include U.S. Pat. Nos. 3,817,837; 3,850,752; 3,939,350; 3,996,345; 4,277,437; 4,275,149; and 4,366,241. See also Handbook of Fluorescent Probes and Research Chemicals (6th Ed., Molecular Probes, Inc., Eugene, Oreg.). Radiolabels can be detected using photographic film or scintillation counters, fluorescent markers can be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

Suitable supports for use in the above methods include, for example, nitrocellulose membranes, nylon membranes, and derivatized nylon membranes, and also particles, such as agarose, a dextran-based gel, dipsticks, particulates, microspheres, magnetic particles, test tubes, microtiter wells, SEPHADEX™ (Amersham Pharmacia Biotech, Piscataway N.J., and the like. Immobilization can be by absorption or by covalent attachment. Optionally, antibodies can be joined to a linker molecule, such as biotin for attachment to a surface.

Solvents used to extract alpha-synuclein from tissue samples can decrease the sensitivity of the assay (e.g., 5M guanidine, urea/thiourea/CHAPS, urea/thiourea, 1% SDS, 1% SDS/8M, cell lysis buffer). It is recommended that such solvents be removed or diluted such that they account for less than 1% and preferably less than 0.1% of the buffer used for the assay.

Preferred pairs of monoclonal antibodies for use in a sandwich assay are an antibody specific for PS129alpha-synuclein as the capture antibody and an antibody binding to an epitope within residues 40-55 of alpha-synuclein as a reporter antibody. Such antibodies detect alpha-synuclein phosphorylated at serine 129. Such antibodies also detect fragments of alpha-synuclein including residues 40-55 and 129 and any additional residues completing the epitope of the PS129-alpha-synuclein-specific antibody. For example, if the capture antibody binds an epitope from 127-131, fragments including at least residue 40 to residue 131 of alpha-synuclein would be detected.

The signal from the reporter assay is usually attributable to full-length PS-129 alpha-synuclein and fragment(s) thereof present in the sample as noted above. Thus, when the assay is said to detect presence or an amount of PS129 alpha-synuclein, the PS129 alpha-synuclein can be full-length or fragments or both. Typically the signal does not resolve between full-length PS-129 alpha-synuclein and its fragments, but their respective contributions can be resolved by eluting from the sandwich complex and subjecting to further analysis, such as by mass spectrometry or gel electrophoresis or mapping with other antibodies.

A preferred implementation of the method has the capture antibody, preferably 11A5, immobilized on magnetic particles, optionally via a linker, such as biotin. The sample is contacted first by the capture antibody, which binds to PS129 alpha-synuclein (if present) in the sample. Complexes formed (if PS129 alpha-synuclein is present) can then be separated from the rest of the sample including unbound proteins and other contaminants by applying a magnetic field. After separation and optionally washing, the capture antibody-PS129 alpha-synuclein complexes linked to the beads are resuspended in a fresh solution. The reporter antibody, preferably 23E8, is then supplied. The reporter antibody preferably bears a fluorescent label. The reporter antibody binds to the complexes of capture antibody-PS129 alpha-synuclein (if PS129 alpha-synuclein is present in the sample) completing the sandwich of capture antibody PS129 alpha-synuclein and reporter antibody. The sandwich complex is then brought out of suspension by reapplying the magnetic field. The complexes can optionally be washed to remove any unbound labeled reporter. The reporter antibody is eluted from the sandwich complexes and detected. Preferably detection is by a single-molecule counting technique, such as one in which fluorescent molecules cross a laser beam in a capillary flow path and individual fluorescent signals are recorded (J Clin Invest. 2015; 125(5):1979-1986. doi:10.1172/JCI80743) A preferred format for this technology is the Erenna® Immunoassay System (EMD Millipore, Billerica, Mass.).

In some methods, the standard PS129 alpha-synuclein and sample are diluted in Singulex standard diluent comprising phosphate-buffered saline and 0.1% bovine serum albumin (BSA). In some methods, the standard PS129 alpha-synuclein and sample are diluted in modified Singulex standard diluent comprising phosphate-buffered saline, 0.1% bovine serum albumin (BSA), and 0.1% Triton X-405. In some methods, a Singulex assay buffer comprising SMC Blocker cocktail, 0.3% Triton X-100, and 150 mM NaCl is used for diluting the antibodies and magnetic particles. Exemplary buffers are disclosed in U.S. Pat. No. 7,572,640.

Some methods also determine total alpha-synuclein or unphosphorylated alpha-synuclein to calculate a ratio of phosphorylated alpha-synuclein to total alpha-synuclein or unphosphorylated alpha-synuclein. Total alpha-synuclein refers to alpha-synuclein irrespective of phosphorylation state. Because PS129 alpha-synuclein usually contributes less than 10% by mass or moles of total alpha-synuclein levels of total alpha-synuclein and unphosphorylated alpha-synuclein are not usually materially different. Total alpha-synuclein can be detected by any method including methods disclosed by U.S. Pat. No. 7,674,599. Optionally, detection is performed with a pair of antibodies having epitope specificity the same or similar to the antibodies used for detecting PS129 alpha-synuclein. The same specificity of reporter antibody can be used (i.e., binding to an epitope within residues 40-55 of alpha-synuclein. The capture antibody can also bind to the same or similar epitope (e.g., a linear epitope spanning, adjacent to or proximate to residue 129) as the capture antibody used for detecting PS129 alpha-synuclein but should not preferentially bind to PS129 alpha-synuclein over unphosphorylated alpha-synuclein. The antibody may or may not preferentially bind to non-phosphorylated alpha-synuclein over PS129 alpha-synuclein. Such a combination of antibodies detects full-length unphosphorylated alpha-synuclein and any fragments thereof including both the reporter and capture antibody binding sites. If the capture antibody binds both PS129 alpha-synuclein and unphosphorylated alpha-synuclein such a combination of antibodies also detects full-length phosphorylated alpha-synuclein and any fragments thereof including both the reporter and capture antibody binding sites.

In some methods, no cross-reactivity with synuclein monomer is observed. In some methods, no cross-reactivity with synuclein monomer is observed at up to 500 pg/mL.

IV. Applications

A. Body Fluids

In vivo detection of PS129 alpha-synuclein in patient samples can be used for diagnosing and monitoring diseases characterized by Lewy bodies or other deposits of alpha-synuclein. Synucleinopathic diseases include Parkinson's disease (PD), dementia with Lewy bodies (DLB), the Lewy body variant of Alzheimer's disease (LBVAD), multiple systems atrophy (MSA), neurodegeneration with brain iron accumulation type-1 (NBIA-1), diffuse Lewy body disease (DLBD), and combined PD and Alzheimer's disease (AD). Suitable patient samples include body fluids, such as blood, CSF, urine, and peritoneal fluid. The presence of a synucleinopathic disease is generally associated with significantly altered levels of PS129 alpha-synuclein in the fluid (typically increased) when compared to the mean values in normal individuals, i.e., individuals not suffering from a synucleinopathic disease. A level is significantly altered if it departs by at least one and preferably at least two standard deviations from the mean level in a population of normal individuals. In some methods, a level of total alpha-synuclein or unphosphorylated alpha-synuclein is also determined and optionally a ratio is calculated between the level of phosphorylated alpha-synuclein and total alpha-synuclein or unphosphorylated alpha-synuclein. Such a ratio generally changes in the same direction as PS129 alpha-synuclein (i.e., increased ratio indicates presence or greater severity of disease).

In some methods, hemoglobin levels in a CSF sample are determined as a measure of red blood cell contamination in order to ensure measurement of neurosynuclein and not synuclein from blood (Kang, J. H., et al., JAMA Neurol. 2013; 70 1277-1287, Hong, Z. et al., Brain 2010, 133:713-726; Barbour, R., et al. Neurodegener Dis, 2008. 5:55-59). In some methods, hemoglobin levels in a CSF sample are determined with a human hemoglobin ELISA assay, e.g., Human Hemoglobin ELISA Quantitation Kit (Bethyl Lab Inc., Montgomery, Tex.). In some methods, hemoglobin levels in a CSF sample are less than 500 ng/mL. In some methods, hemoglobin levels in a CSF sample are 200 ng/mL to 500 ng/mL. In some methods, hemoglobin levels in a CSF sample are less than 200 ng/mL.

In some methods, a CSF sample is diluted 1:4 in modified Singulex standard diluent comprising phosphate-buffered saline, 0.1% bovine serum albumin (BSA), and 0.1% Triton X-405.

In addition to initial diagnosis of synucleinopathic disease optionally in combination with other signs or symptoms of disease, PS129 alpha-synuclein or the ratios discussed above can be monitored to follow the progress of the disease by measuring PS129 alpha-synuclein at multiple times, such as before and during treatment, thereby following the effectiveness of treatment, such as immunotherapy against alpha-synuclein. Levels of PS129 alpha-synuclein reverting toward the mean in a population of normal individuals is an indication the treatment regime is effective, and an increased level of PS129 alpha-synuclein is an indication the treatment is not effective.

Presence or levels of PS129 alpha-synuclein or the related ratios discussed above can also be used as a factor in determining future treatment. Subjects in which PS129 alpha-synuclein is present or at a level meeting or exceeding a threshold are indicated as being suitable for treatment or prophylaxis of Lewy body disease (e.g., by immunotherapy) whereas subjects in which PS129 alpha-synuclein is not present or below a threshold are indicated as not being suitable. Although presence or level of PS129 alpha-synuclein may be only one of several signs or symptoms of Lewy body disease affecting a treatment decision, subjects in which PS129 alpha-synuclein is present or at or above the threshold are statistically at a greater likelihood of receiving treatment for a Lewy body disease than subjects in which PS129 alpha-synuclein is absent or below the threshold.

B. Cell Culture

In vitro monitoring of PS129 alpha-synuclein in conditioned culture medium from a suitable cell culture can be used for analyzing processing, phosphorylation and secretion of PS129 alpha-synuclein and the effect of potential agents on the same. Monitoring phosphorylation of alpha-synuclein provides a means to identify phosphorylases responsible for the same. Agents that inhibit processing and/or secretion of PS129 alpha-synuclein have pharmacological activity potentially useful for prophylaxis of synucleinopathic disease. Typically, inhibitory activity is determined by comparing levels of PS129 alpha-synuclein in medium from a cell treated with a test agent versus a comparable control cell not treated with the agent.

Suitable cells include cells transfected with nucleic acids encoding alpha-synuclein, preferably, human alpha-synuclein and cells naturally expressing alpha-synuclein, also preferably human. The alpha-synuclein in transfected cells can bear a mutation, such as S129A, S129D, A53T and A20P. Cells include PeakS cells, SY5Y cells, human cortical cells, human neuroglioma cell lines, human HeLa cells, primary human endothelial cells (e.g. HUVEC cells), primary human fibroblasts or lymphoblasts, primary human mixed brain cells (including neurons, astrocytes, and neuroglia), Chinese hamster ovary (CHO) cells, and the like. SY5Y cells are neuronal cells that can be induced to differentiate by treatment with retinoic acid/BDNF (brain derived neurotrophic factor). Transfected cells expressing PS129 alpha-synuclein at higher levels than normal human cells are preferred.

Random libraries of peptides or other compounds can also be screened for suitability. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated herein by reference for all purposes). Peptide libraries can also be generated by phage display methods. See, e.g., Devlin, WO 91/18980. The test compounds are typically administered to the culture medium at a concentration in the range from about 1 nM to 1 mM, usually from about 10 µM to 1 mM. Test compounds which are able to inhibit formation, processing or secretion of alpha-synuclein are candidates for further determinations in transgenic animals and eventually human clinical trials.

C. Transgenic Animals

The antibodies of the invention and assays for detecting them can also be used to monitor PS129 alpha-synuclein production, phosphorylation and processing in transgenic animal models of disease. Transgenic animal models of Lewy body disease are described by Masliah, et al. Science 287:1265-1269 (2000); Masliah et al., PNAS USA 98:12245-12250 (2001). Alpha synuclein can be analyzed either in body fluids as described above for human samples, or in tissue samples taken directly from the animal (see copending 60/423,012, filed Nov. 1, 2002, incorporated by reference). Tissue samples can be classified as Lewy body, particulate fraction and soluble fractions. Simple assays can be performed as for cell culture to screen agents for capacity to inhibit formation of PS129 alpha-synuclein. Typically, the inhibitory activity is determined by comparing the level of PS129 alpha-synuclein thereof in a particularly body fluid or fraction from a tissue sample from a transgenic animal treated with the agent in comparison with the level of PS129 alpha-synuclein in the same body fluid or fraction in a control transgenic animal not treated with the agent. Inhibitory activity is shown by decreased levels of PS129 alpha-synuclein thereof in the treated animal relative to the control.

Tissue samples from the brains of human patients can be subject to similar analyses. However, as obtaining samples from the brains of patient is an undesirably invasive procedure, such analyses are usually confined to cadavers.

V. Kits

The invention further provides kits including pairs of capture and reporter one or more antibodies of the invention. In some kits the capture antibody is preimmobilized to a solid phase, such as a microtiter dish. Optionally, labeling reagents, such as an antiidiotypic antibody are also included in the kits. The labeling may also include a chart or other correspondence regime correlating levels of measured label with levels of antibodies to alpha-synuclein. The term labeling refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits. The kits can be sold, for example, as research or diagnostic reagents.

Although the invention has been described in detail for purposes of clarity of understanding, it will be obvious that certain modifications may be practiced within the scope of the appended claims. All publications and patent documents cited in this application are hereby incorporated by reference in their entirety for all purposes to the same extent as if each were so individually denoted. Unless otherwise apparent from the context any embodiment, aspect, feature or step can be used in combination with any other. If the content associated with a citation or accession number of the like should change with time, the version existing at the effective filing date of this application is intended, the effective filing date being the actual filing date or earlier filing date of a priority application disclosing the citation or accession number.

EXAMPLES

The examples use the following antibodies:
11A5 (JH22-11A5) epitope AYEMP(phospho)SEEGYQ (Syn124-134).
4B12 (pan alpha-syn) Commercial epitope NEEGAP(Syn 103-108)
MJFR1 (pan alpha-syn) Commercial epitope VDPDNE (Syn 118-123)
23E8 (JH19-23E8) epitope VGSKTKEGVVHGVATV-GGC (Syn 40-55)

Example 1: Preparation of Recombinant PS129 Alpha-Synuclein Standard

Recombinant PS129 alpha-synuclein was prepared using the following method.

Phosphorylation with PLK2 (Conditions adapted from Salvi, M., Trashi, E., Cozza, G., Negro, A., Hanson, P. I., Pinna, L. A. (2012). Biotechniques. Doi: 10.2144/000113866)

Materials:
1) PLK2 Biosciences, Cat #05-158)
2) Recombinant purified alpha-synuclein *E. coli* expressed protein prepared using a boiling/anion exchange method or a NiNTA/anion exchange method prepared without heat 3) 10×PLK2 reaction buffer (freshly prepared)
   200 mM Tris pH 7.5
   100 mM $MgCl_2$
   10 mM DTT
4) ATP Stock (with very limited freeze-thaw history), 10 mM, (ATP from New England Biolabs)

Reaction:
1) Prepare alpha-synuclein. (1.25 mg alpha-synuclein, prepared to a concentration of <3.5 mg/mL.) Final reaction volume was 0.5 mL.
2) Buffer-exchange concentrated alpha-synuclein into $ddH_2O$.
3) Assemble reaction. For a standard 0.5 ml reaction, the final reaction mixture:
   1×PLK2 buffer
   25 µM ATP
   1.25 mg alpha-synuclein
   5 µg PLK2 (1:250 kinase: substrate ratio)
   $ddH_2O$ to 0.5 mL
4) Incubate overnight at 30° C.
5) Optional: next morning, boil sample to precipitate kinase (not necessary if chromatography step is followed. PLK2 will resolve from phospho-synuclein).

Chromatographic separation of phosphorylated synuclein
For resolution of phosphorylated synuclein from the kinase reaction mixture, the following conditions were used: a slow salt gradient on a 1 mL Q HP HiTrap column (GE Lifesciences), using an AKTA Purifier. Using the conditions below, the proteinaceous non-phosphorylated and phosphorylated peaks, and PLK2, as well as non-proteinaceous ATP and ADP, were resolved.

Buffer A: 20 mM Tris pH 7.5
Buffer B: 20 mM Tris pH 7.5 with 1M NaCl
Sample: Diluted 2:1 with loading buffer (i.e. 2× sample volume added to sample)
Flow rate: 1 ml/min
Wash with 3 CV Buffer A
Step to 20% B, wash with 3 CV
Gradient: 20-55% B over 35 CV
For the first time running, may run lower, slower gradient to verify successful resolution.
Elution peaks by conductance:
ADP: 16 mS/cm
ATP: 18.3 mS/cm
Non-phosphorylated Synuclein 25.7 mS/cm
Phospho-synuclein: 28.4 mS/cm Phospho-synuclein peak was collected and dialyzed into PBS before freezing. A non-phosphorylated control was run to verify elution peaks. The method resolves phosphorylated from non-phosphorylated synuclein by charge, but not according to phosphorylation site. Mass spectrometry of purified material showed most phosphorylation is at pS129 and minor secondary phosphorylation at T33 and T81.

Example 2 Assay for Detecting PS129 Alpha-Synuclein

Recombinant PS129 alpha-synuclein prepared as in Example 1 was used as a target for detection.

A feasibility protocol was followed to determine the range of PS129 alpha-synuclein determined by different antibody combinations. Briefly, the protocol included 6-point 10-fold diluted standard curves for six antibody permutations to tests each pair's potential and the estimate the analyte concentrations to be used in subsequent experiments. 100 µL of standard PS129 alpha-synuclein sample diluted in Singulex standard diluent (comprising phosphate-buffered saline and 0.1% bovine serum albumin (BSA)) was mixed with 100 µL of Singulex assay buffer (comprising SMC Blocker cocktail, 0.3% Triton X-100, and 150 mM NaCl) containing magnetic particles coated with the capture antibody and incubated 120 min at 25° C. The 11A5 antibody was attached to magnetic particles via a biotin linker. Bound analyte was then washed utilizing magnetic separation to keep the MPs isolated during to the wash procedures to ensure no loss of beads. After washing and removing any excess buffer, 20 µL of detection antibody in Singulex assay buffer was added and incubated 60 min at 25° C. The resulting complexes were washed four times using magnetic separation, as above. Singulex Elution buffer (Elution Buffer B, Catalog No. 02-0297-00, EMD Millipore, Billerica, Mass.) was added and incubated for 5-10 min at 25° C. The eluate was transferred to a 384-well plate containing Singulex neutralization buffer (Buffer D, Catalog No. 02-0368-00, EMD Millipore, Billerica, Mass.). The 384-well plate was then read using the Erenna® Immunoassay System utilizing single molecule counting (SMC™) technology.

Tables 1 and 2 show the sensitivity of detection of various combinations of capture and reporter antibody. The combination of 11A5 as the capture antibody and 23E8 as the reporter antibody showed about 10-fold greater sensitivity than any other combination having a lower limit of quantification (LLOQ) of about 0.1 pg/mL (~7 fM).

TABLE 1

Phospho-α-Synuclein: Feasibility Range-Pan Capture

| Capture | Detection | Expected [PS129] pg/mL | n | DE mean | SD | CV % | bkgrd | SD | slope DE/pg/mL | Estimated LLOQ pg/mL | mean [PS129] pg/mL | SD | CV % | Recovery |
|---|---|---|---|---|---|---|---|---|---|---|---|---|---|---|
| 4B12 | PRT-11A5 | 1000.00 | 2 | 12940 | 100 | 1 | 82 | 4 | 17 | 5.00 | 1002.12 | 44.11 | 4 | 100% |
|  |  | 100.00 | 2 | 1830 | 59 | 3 |  |  |  |  | 100.13 | 3.47 | 3 | 100% |
|  |  | 10.00 | 2 | 271 | 16 | 6 |  |  |  |  | 10.05 | 0.86 | 9 | 101% |
|  |  | 1.00 | 2 | 100 | 10 | 10 |  |  |  |  | 1.07 | 0.27 | 25 | 107% |
|  |  | 0.10 | 2 | 84 | 11 | 13 |  |  |  |  | ND | — | — | — |
|  |  | 0.00 | 2 | 82 | 4 | 4 |  |  |  |  | ND | — | — | — |
| MJFR1 | PRT-11A5 | 1000.00 | 2 | 11813.5 | 241 | 2 | 56 | 11 | 58 | 1.00 | 1001.63 | 37.41 | 4 | 100% |
|  |  | 100.00 | 2 | 5223 | 98 | 2 |  |  |  |  | 98.79 | 2.53 | 3 | 99% |
|  |  | 10.00 | 2 | 639 | 3 | 0 |  |  |  |  | 10.14 | 0.04 | 0 | 101% |
|  |  | 1.00 | 2 | 115 | 2 | 2 |  |  |  |  | 0.93 | 0.04 | 4 | 93% |
|  |  | 0.10 | 2 | 69 | 3 | 4 |  |  |  |  | ND | — | — | — |
|  |  | 0.00 | 2 | 56 | 11 | 20 |  |  |  |  | ND | — | — | — |
| PRT-23E8 | PRT-11A5 | 1000.00 | 2 | 13600 | 21 | 0 | 41 | 5 | 26 | 1.00 | 1006.30 | 66.07 | 7 | 101% |
|  |  | 100.00 | 2 | 2672 | 59 | 2 |  |  |  |  | 99.88 | 2.21 | 2 | 100% |
|  |  | 10.00 | 2 | 337 | 21 | 6 |  |  |  |  | 10.03 | 0.72 | 7 | 100% |
|  |  | 1.00 | 2 | 75 | 7 | 9 |  |  |  |  | 1.03 | 0.23 | 22 | 103% |
|  |  | 0.10 | 2 | 44 | 6 | 13 |  |  |  |  | ND | — | — | — |
|  |  | 0.00 | 2 | 41 | 5 | 12 |  |  |  |  | ND | — | — | — |

TABLE 2

Phospho-α-Synuclein: Feasibility Range-p-Syn capture

| Capture | Detection | Expected [PS129] pg/mL | n | DE mean | SD | CV % | bkgrd | SD | slope DE/pg/mL | Estimated LLOQ pg/mL | mean [PS129] pg/mL | SD | CV % | Recovery |
|---|---|---|---|---|---|---|---|---|---|---|---|---|---|---|
| PRT-11A5 | 4B12 | 1000.00 | 2 | 12187 | 506 | 4 | 69 | 46 | 17 | 5.00 | 1013.47 | 78.71 | 8 | 101% |
|  |  | 100.00 | 2 | 1698 | 45 | 3 |  |  |  |  | 100.08 | 2.83 | 3 | 100% |
|  |  | 10.00 | 2 | 215 | 53 | 25 |  |  |  |  | 10.67 | 3.14 | 29 | 107% |
|  |  | 1.00 | 2 | 52 | 1 | 1 |  |  |  |  | ND | — | — | — |
|  |  | 0.10 | 2 | 35 | 6 | 16 |  |  |  |  | ND | — | — | — |
|  |  | 0.00 | 2 | 69 | 46 | 67 |  |  |  |  | ND | — | — | — |
| PRT-11A5 | MJFR1 | 1000.00 | 2 | 10104 | 26 | 0 | 36 | 6 | 60 | 1.00 | 1000.10 | 7.30 | 1 | 100% |
|  |  | 100.00 | 2 | 7637 | 962 | 13 |  |  |  |  | 101.49 | 17.16 | 17 | 101% |
|  |  | 10.00 | 2 | 636 | 6 | 1 |  |  |  |  | 10.02 | 0.08 | 1 | 100% |
|  |  | 1.00 | 2 | 96 | 12 | 13 |  |  |  |  | 1.20 | 0.27 | 22 | 120% |
|  |  | 0.10 | 2 | 44 | 8 | 19 |  |  |  |  | ND | — | — | — |
|  |  | 0.00 | 2 | 36 | 6 | 16 |  |  |  |  | ND | — | — | — |
| PRT-11A5 | PRT-23E8 | 1000.00 | 2 | 9664 | 842 | 9 | 26 | 8 | 549 | 0.05 | 1000.78 | 27.54 | 3 | 100% |
|  |  | 100.00 | 2 | 12151 | 48 | 0 |  |  |  |  | 100.70 | 2.72 | 3 | 101% |
|  |  | 10.00 | 2 | 4457 | 309 | 7 |  |  |  |  | 9.89 | 0.90 | 9 | 99% |
|  |  | 1.00 | 2 | 580 | 18 | 3 |  |  |  |  | 1.01 | 0.03 | 3 | 101% |
|  |  | 0.10 | 2 | 92 | 5 | 5 |  |  |  |  | 0.10 | 0.01 | 9 | 100% |
|  |  | 0.00 | 2 | 26 | 8 | 31 |  |  |  |  | ND | — | — | — |

The screening assays suggested the following protocol using 11A5 as the capture and 23E8 as the reporter antibody.

Add 100 μL it standard PS129 alpha-synuclein+100 μL magnetic particles (MPs) coated with antibody 11A5
Incubate 120 min at 25° C.
Wash 1× using magnetic separation
Add 20 μL of detection antibody 23E8 and incubate 60 min at 25° C.
Wash 4× using magnetic separation
Add elution buffer and incubate for 5-10 min at 25° C.
Transfer eluate to 384-well plate containing neutralization buffer
Read 384-well plate in Erenna FIG. 1 and Table 3 show sensitivity of detection 11A5 as the capture antibody and 23E8 as the reporter antibody with different amounts of the capture antibody in the wells. 5 μg of MPs coated with capture antibody per well of capture antibody is preferred because the resulting slope of signal versus PS-129 alpha-synuclein concentration has an extended linear portion in the high sensitivity range.

TABLE 3

PS129: LLOQ Estimation in Singulex Standard Diluent

| MP Mass Per Well | Expected [PS129] pg/mL | n | DE mean | SD | CV % | mean [PS129] pg/mL | SD | CV % | Recovery % | bkgrd | SD | slope DE/pg/mL | LoD pg/mL |
|---|---|---|---|---|---|---|---|---|---|---|---|---|---|
| 10 ug MP | 25.00 | 2 | 12547 | 357 | 3 | 22.55 | 2.28 | 10 | 90 | 139 | 18 | 2421 | 0.015 |
|  | 12.50 | 3 | 12830 | 234 | 2 | 13.47 | 0.56 | 4 | 108 |  |  |  |  |
|  | 6.25 | 3 | 9890 | 183 | 2 | 6.56 | 0.10 | 2 | 105 |  |  |  |  |
|  | 3.13 | 3 | 6168 | 729 | 12 | 3.02 | 0.50 | 16 | 97 |  |  |  |  |
|  | 1.56 | 3 | 3402 | 124 | 4 | 1.43 | 0.06 | 4 | 92 |  |  |  |  |
|  | 0.78 | 3 | 2361 | 392 | 17 | 0.93 | 0.18 | 19 | 119 |  |  |  |  |
|  | 0.39 | 3 | 1151 | 159 | 14 | 0.41 | 0.07 | 16 | 106 |  |  |  |  |
|  | 0.20 | 2 | 568 | 88 | 16 | 0.17 | 0.04 | 21 | 88 |  |  |  |  |
|  | 0.10 | 2 | 396 | 4 | 1 | 0.10 | 0.00 | 0 | 102 |  |  |  |  |
|  | 0.05 | 3 | 351 | 136 | 39 | 0.08 | 0.06 | 67 | 170 |  |  |  |  |
|  | 0.02 | 3 | 265 | 100 | 38 | 0.33 | 0.34 | 103 | 1356 |  |  |  |  |
|  | 0.00 | 3 | 139 | 18 | 13 | ND | — | — | — |  |  |  |  |
| 5 ug MP | 25.00 | 3 | 13070 | 246 | 2 | 25.62 | 0.81 | 3 | 102 | 93 | 18 | 1044 | 0.034 |
|  | 12.50 | 3 | 9798 | 269 | 3 | 12.65 | 0.51 | 4 | 101 |  |  |  |  |
|  | 6.25 | 3 | 5968 | 326 | 5 | 6.47 | 0.39 | 6 | 104 |  |  |  |  |
|  | 3.13 | 3 | 3036 | 192 | 6 | 2.97 | 0.39 | 13 | 95 |  |  |  |  |
|  | 1.56 | 3 | 1696 | 133 | 8 | 1.48 | 0.13 | 9 | 95 |  |  |  |  |
|  | 0.78 | 2 | 991 | 10 | 1 | 0.82 | 0.01 | 1 | 105 |  |  |  |  |
|  | 0.39 | 3 | 548 | 36 | 7 | 0.42 | 0.03 | 8 | 108 |  |  |  |  |
|  | 0.20 | 3 | 308 | 12 | 4 | 0.21 | 0.01 | 5 | 107 |  |  |  |  |
|  | 0.10 | 2 | 167 | 13 | 8 | 0.08 | 0.01 | 15 | 83 |  |  |  |  |
|  | 0.05 | 3 | 165 | 57 | 34 | 0.08 | 0.05 | 66 | 162 |  |  |  |  |
|  | 0.02 | 2 | 117 | 10 | 8 | 0.03 | 0.01 | 27 | 143 |  |  |  |  |
|  | 0.00 | 3 | 93 | 18 | 19 | ND | — | — | — |  |  |  |  |

PS129: Summary and Conclusions

Figure 2C:
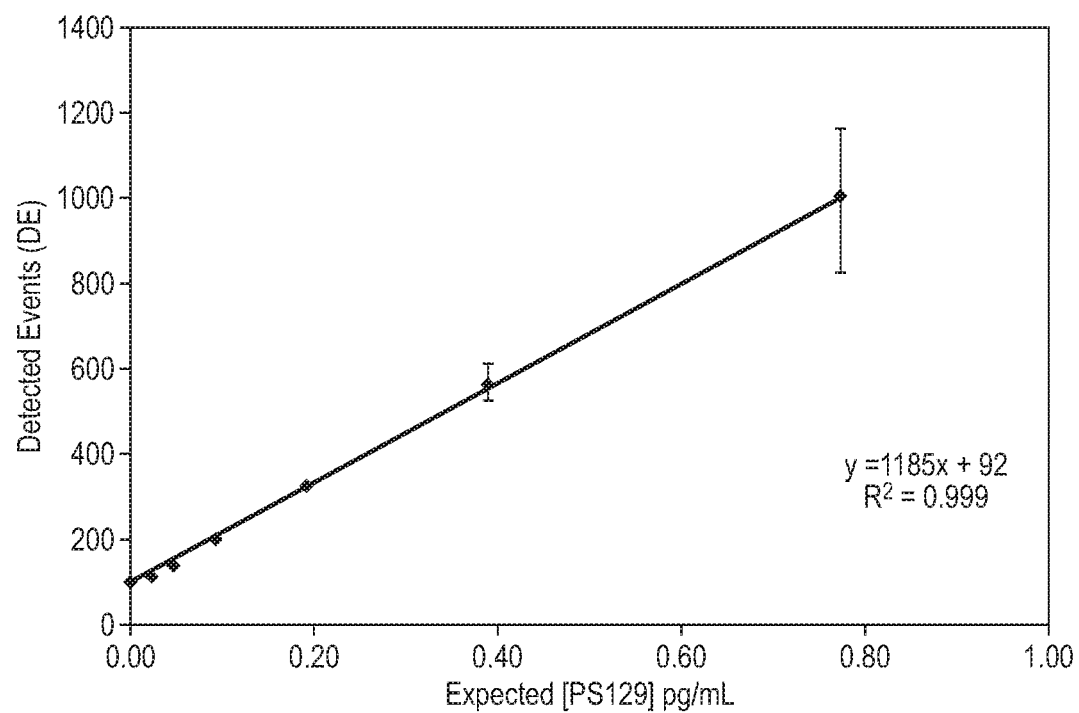

A LLOQ of 0.1 pg phosphorylated alpha-synuclein per mL was detected with 11A5 at 5 μg magnetic particles per well coated at 12.5 μg IgG per mg magnetic particles and 23E8 at 2,000 ng/mL. Using the preferred antibody combination at their preferred amounts a calibration curve was determined relating signal to PS129 alpha-synuclein concentration as shown in FIGS. 2A-C. The standard curve has a detection range of 25 pg/mL-0.02 pg/mL.

The 12-pt curve in FIG. 2A is used to interpolate PS129 alpha-synuclein levels from samples. It is a dilutional series (in this case 2-fold for 11-pts with a zero anchor). The highlighted section is what was determined as the low end sensitivity of the assay, while the Lower Limit of Quantification (LLOQ) which is defined as the lowest point with ≤20% CV and recovery between 80-120% of expected (and a signal of >1.5× the background signal (e.g. the value at the 0 point) shown here as 0.1 pg/mL. The low-end curve (2B) is just an expanded area of the high sensitivity area looking only at the DE signal of the linear segment (e.g. <1000 DE) where the DE signal is virtually 100% contribution to the determination of the concentration. FIG. 2C is a graphical representation of the high sensitivity area showing linearity across the lowest concentrations (a plot of the upper right data).

Levels of PS129 alpha-synuclein were then measured in neurological control samples of CSF with and without spiking with PS129 alpha-synuclein (Table 4).

A lower limit of detection (LOD) of 0.05 pg PS129 alpha-synuclein per mL and a lower limit of quantification (LLOQ) of 0.1 pg PS129 alpha-synuclein per mL were detected with the optimized assay.

Normal CSF samples were tested in the optimized assay. Hemoglobin concentration in CSF samples was determined prior to dilution in modified Singulex standard diluent.

TABLE 4

| ID | Neurological Control | Spike | Measured | Dilution Corrected | CV | Recovered | % Recovery | Total Synuclein | % PS129 |
|---|---|---|---|---|---|---|---|---|---|
| 621 | Concussion | 0 | 0.58 | 1.17 | 11 | 5.53 | 111 | 222.83 | 0.5 |
|  |  | 5 | 3.35 | 6.7 | 11 |  |  |  |  |
| 633 | MS | 0 | 6.03 | 12.06* | 24 | 5.39 | 108 | 3075.77* | 0.4 |
|  |  | 5 | 8.73 | 17.45 | 3 |  |  |  |  |
| 696 | MS | 0 | 1.21 | 2.43 | 11 | 5.90 | 118 | 414.54 | 0.6 |
|  |  | 5 | 4.16 | 8.32 | 2 |  |  |  |  |
| 623 | Optic Neuritis | 0 | 14.44 | 28.88 | 12 | 5.17 | 103 | 529.19 | 5.4 |
|  |  | 5 | 17.03 | 34.05 | 3 |  |  |  |  |
| 693 | PSP | 0 | 1.24 | 2.49 | 16 | 7.41 | 148 | 225.48 | 1.1 |
|  |  | 5 | 4.95 | 9.90 | 3 |  |  |  |  |

Example 3: Optimized Assay for Detecting PS129 Alpha-Synuclein in CSF

An optimized assay for detecting PS129 alpha-synuclein in CSF samples uses a modified Singulex standard diluent (comprising phosphate-buffered saline, 0.1% bovine serum albumin (BSA), and 0.1% Triton X-405) in the assay of Example 2. CSF samples in the optimized assay are diluted 1:4 in modified Singulex standard diluent prior to use.

Figures 3A, 3B, 3C:
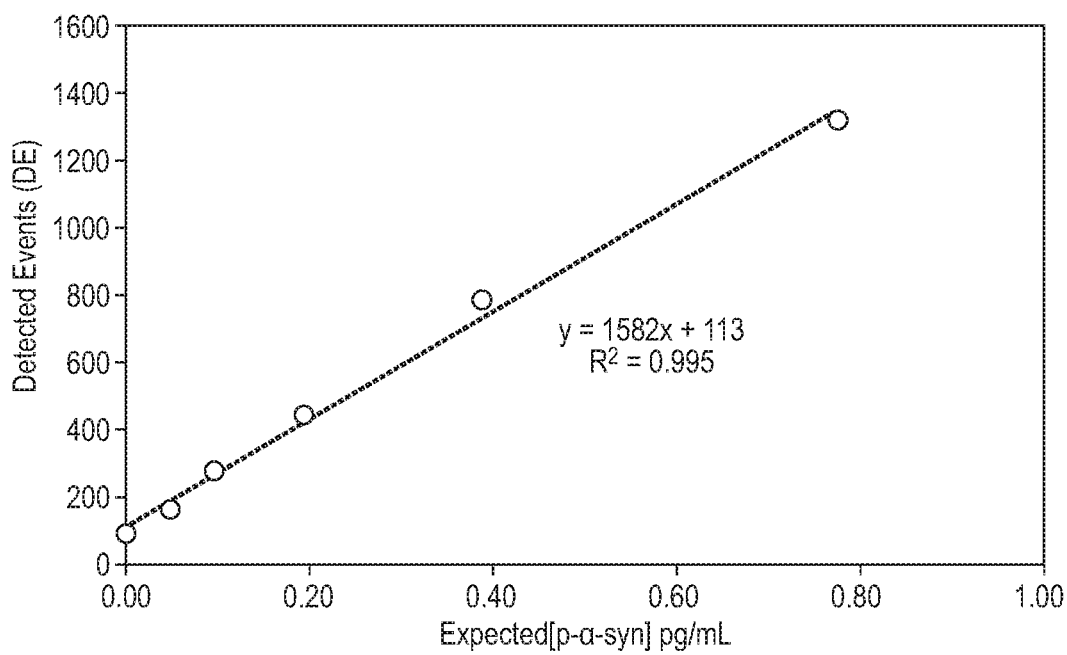
FIGS. 3A-C show determination, in an assay using Singulex standard diluent comprising 0.1% Triton X-405, of a calibration curve relating signal to PS129 alpha-synuclein concentration (A) 12 point PS129 alpha-synuclein standard curve, B low end plotting actual values (mean detection events) and C, linear plot.

A calibration curve was determined relating signal to PS129 alpha-synuclein concentration as shown in FIGS. 3A-C. The standard curve has a detection range of 50 pg/mL-0.05 pg/mL. The 12-pt curve in FIG. 3A is used to interpolate PS129 alpha-synuclein-levels from samples. It is a dilutional series (in this case 2-fold for 11-pts with a zero anchor) of reference PS129 alpha-synuclein diluted in modified Singulex standard diluent. The highlighted section is what was determined as the Lower Limit of Quantification (LLOQ) which is defined as the lowest point with ≤20% CV and recovery between 80-120% of expected (and a signal of >1.5× the background signal (e.g. the value at the 0 point). The low-end curve (3B) is just an expanded area of the high sensitivity area looking only at the DE signal of the linear segment (e.g. <1000 DE) where the DE signal is virtually 100% contribution to the determination of the concentration. FIG. 3C is a graphical representation of the high sensitivity area showing linearity across the lowest concentrations (a plot of the upper right data).

CSF samples were diluted at least 1:4 in modified Singulex standard diluent prior to the PS129 alpha-synuclein assay. An LLOQ of 0.4 pg/mL PS129 alpha-synuclein (in the undiluted CSF) was detected with the optimized assay with 1:4 dilution of the CSF.

The assay was performed with several CSF samples and passed industry standards of intra assay variability, inter assay variability, spike and recovery and cross-reactivity, linearity and parallelism.

Spiking the undiluted CSF samples with monosynuclein at up to 500 pg/mL showed no interference with detection of PS129 alpha-synuclein in the optimized assay. Monosynuclein signals (at up to 500 pg/mL) were below the LLOQ. Using the Meso Scale Diagnostics Synuclein assay (Meso Scale Diagnostics Human α-Synuclein Kit (Cat. # K151TGD-2, Meso Scale Diagnostics, Rockville, Md.) synuclein levels were found to be in the 10-500 pg/mL range provided there was not contamination from red blood cells which are known to contain significant amounts of synuclein. (Barbour, 2008). Therefore at expected levels of synuclein there is no cross-reactivity. BIAcore experiments with antibody 11A5 also showed no cross-reactivity with monosynuclein at up to μM level.

What is claimed is:

1. A method of detecting alpha-synuclein phosphorylated at serine 129 (PS129 alpha-synuclein), comprising:
    (a) contacting a sample with a capture antibody that preferentially binds to PS129 alpha-synuclein and a reporter antibody that specifically binds to an epitope within residues 40-55 of alpha-synuclein, wherein the capture antibody comprises the Kabat CDRs of 11A5 (ATCC accession number PTA-8222) and the reporter antibody comprises the Kabat CDRs of 23E8 (ATCC accession number PTA-122711); wherein if PS129 alpha-synuclein is present in the sample, the capture antibody and reporter antibody bind to the PS129 alpha-synuclein forming a sandwich complex; and
    (b) detecting the reporter antibody that binds to the PS129 alpha-synuclein in step (a), if any, to indicate presence or absence of the PS129 alpha-synuclein.

2. The method of claim 1, wherein the capture antibody is 11A5 and the reporter antibody is 23E8.

3. The method of claim 1, wherein the capture antibody is attached to a support via a linker.

4. The method of claim 3, wherein the capture antibody is bound to the support before the contacting step.

5. The method of claim 3, wherein the support is magnetic beads.

6. The method of claim 5, wherein the capture antibody is attached to magnetic beads, which are separated from the remainder of the sample or resuspended solution by applying a magnetic field.

7. The method of claim 1, further comprising eluting the reporter antibody from the sandwich complex before detecting the reporter antibody.

8. The method of claim 1, wherein the reporter antibody is fluorescently labeled, and is detected by single-molecule counting.

9. The method of claim 1, wherein the sample is contacted with the capture antibody, the capture antibody binds to PS129 alpha-synuclein, the capture antibody bound to PS129 alpha-synuclein is separated from other components of the sample and resuspended in solution, which is contacted with the reporter antibody, which binds to the PS129 alpha-synuclein forming the sandwich complex, which is separated from other components of the resuspended solution, and the reporter antibody is eluted from the sandwich complex and detected.

10. The method of claim 1, performed qualitatively.

11. The method of claim 1, performed quantitatively to indicate an absolute or relative amount of the PS129 alpha-synuclein.

12. The method of claim 1, wherein the sample contains 0.1-1.0 M guanidine.

13. The method of claim 12, wherein the sample contains 0.5 M guanidine.

14. The method of claim 1, further comprising: comparing a signal from the reporter antibody with a signal from the reporter antibody in a control sample containing a known amount of PS129 alpha-synuclein to determine the amount of PS129 alpha-synuclein in the sample.

15. The method of claim 1, further comprising comparing a signal from the reporter antibody from a calibration curve of signal versus amount of PS129 alpha-synuclein to determine the amount of PS129 alpha-synuclein in the sample.

16. The method of claim 1, wherein a signal from the reporter antibody is proportional to the amount of PS129 alpha-synuclein in the sample.

17. The method of claim 1, further comprising contacting the reporter antibody with a labeled antibody to generate a signal indicating presence of the reporter antibody and thereby presence of PS129 alpha-synuclein in the sample.

18. The method of claim 1, further comprising determining a level of total alpha-synuclein or unphosphorylated alpha-synuclein in the sample and calculating a ratio of the level of phosphorylated alpha-synuclein to the level of total alpha-synuclein or unphosphorylated alpha-synuclein.

19. The method of claim 1, wherein the sample is diluted in Singulex standard diluent comprising 0.1% Triton X-405.

20. The method of claim 1, wherein the sample is a sample from a human.

21. The method of claim 1, wherein the sample from a transgenic mouse with a transgene expressing human alpha-synuclein.

22. The method of claim 1, wherein the sample is a body fluid.

23. The method of claim 22, wherein the sample is cerebrospinal fluid (CSF) of a human.

24. The method of claim 23, wherein the CSF sample is diluted 1:4 in Singulex standard diluent comprising 0.1% Triton X-405.

25. The method of claim 24, which detects presence of PS129 alpha-synuclein at a level of at least 0.4 pg/mL.

26. The method of claim 1, wherein there is no cross-reactivity with synuclein monomer at up to 500 pg/mL.

27. The method of claim 23, wherein the CSF sample comprises <500 ng/mL hemoglobin.

28. The method of claim 23, wherein the CSF sample comprises 200 ng/mL to 500 ng/mL hemoglobin.

29. The method of claim 23, wherein the CSF sample comprises <200 ng/mL hemoglobin.

30. The method of claim 1, wherein the sample is a brain homogenate of a human or transgenic animal.

31. The method of claim 1, wherein the sample is a medium used to culture cells.

32. The method of claim 31, wherein the cells express recombinant human alpha-synuclein.

33. The method of claim 1, which detects presence of PS129 alpha-synuclein at a level of 0.1 pg/mL.

34. The method of claim 1, wherein presence of PS129-alpha-synuclein is used to diagnose a subject from whom the sample was obtained with Lewy body disease.

35. The method of claim 1, performed on a population of subjects, wherein a greater proportion of subjects with presence of PS129 alpha-synuclein thereafter receive a treatment for Lewy body disease than subjects with absence of PS129-alpha synuclein.

36. The method of claim 1, performed on a population of subjects, wherein a greater proportion of subject with a level of PS129 alpha-synuclein at or exceeding a threshold receive treatment for a Lewy body disease than subjects in which the level of PS129 alpha-synuclein is below the threshold.

37. A monoclonal antibody comprising the Kabat CDRs of 23E8 (ATCC accession number PTA-122711).

38. The monoclonal antibody of claim 37 that is chimeric, veneered or humanized.

\* \* \* \* \*

UNITED STATES PATENT AND TRADEMARK OFFICE
CERTIFICATE OF CORRECTION

PATENT NO. : 10,852,309 B2
APPLICATION NO. : 15/247598
DATED : December 1, 2020
INVENTOR(S) : Robin Barbour et al.

Page 1 of 1

It is certified that error appears in the above-identified patent and that said Letters Patent is hereby corrected as shown below:

In the Claims

Column 24, Claim 21, Line 56, after "sample" insert --is--

Column 26, Claim 36, Line 8, delete "subject" and insert --subjects--

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 1

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Gly Lys
            20                  25                  30
```

-continued

```
Thr Lys Glu Gly Val Leu Tyr Val Gly Ser Lys Thr Lys Glu Gly Val
    35                      40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65              70                  75                      80

Thr Val Glu Gly Ala Gly Ser Ile Ala Ala Thr Gly Phe Val Lys
            85                  90                  95

Lys Asp Gln Leu Gly Lys Asn Glu Glu Gly Ala Pro Gln Glu Gly Ile
            100             105             110

Leu Glu Asp Met Pro Val Asp Pro Asp Asn Glu Ala Tyr Glu Met Pro
        115             120                 125

Ser Glu Glu Gly Tyr Gln Asp Tyr Glu Pro Glu Ala
    130             135             140
```